(12) United States Patent
Kang et al.

(10) Patent No.: US 9,158,048 B2
(45) Date of Patent: Oct. 13, 2015

(54) DIIMMONIUM-BASED COMPONENT AND NEAR INFRARED ABSORPTION FILTER USING SAME

(75) Inventors: Ju-Sik Kang, Hwaswong-Si (KR); Jeong-Ho Park, Suwon-Si (KR); Yu-Mi Chang, Gwangju-Si (KR)

(73) Assignee: SK CHEMICALS CO., LTD., Seongnam-Si (KR)

( * ) Notice: Subject to any disclaimer, the term of this patent is extended or adjusted under 35 U.S.C. 154(b) by 0 days.

(21) Appl. No.: 13/976,600

(22) PCT Filed: Dec. 26, 2011

(86) PCT No.: PCT/KR2011/010082
§ 371 (c)(1),
(2), (4) Date: Aug. 27, 2013

(87) PCT Pub. No.: WO2012/091379
PCT Pub. Date: Jul. 5, 2012

(65) Prior Publication Data
US 2013/0331608 A1 Dec. 12, 2013

(30) Foreign Application Priority Data
Dec. 28, 2010 (KR) .................. 10-2010-0136942

(51) Int. Cl.
*C07C 251/30* (2006.01)
*C07F 5/04* (2006.01)
*G02B 5/22* (2006.01)
*G02B 5/20* (2006.01)

(52) U.S. Cl.
CPC ............ *G02B 5/22* (2013.01); *C07C 251/30* (2013.01); *C07F 5/04* (2013.01); *G02B 5/208* (2013.01)

(58) Field of Classification Search
CPC ........ C07C 251/30; C07F 5/022; C07F 5/025; G02B 5/208; G02B 5/22

USPC .................................................. 564/8; 568/6
See application file for complete search history.

(56) References Cited

U.S. PATENT DOCUMENTS

2007/0123614 A1  5/2007  Nakabeppu et al.
2010/0208337 A1*  8/2010  Uehara et al. ............. 359/359

FOREIGN PATENT DOCUMENTS

| JP | 2007246464 A | 9/2007 | |
| JP | 2008528706 A | 7/2008 | |
| KR | 1020070053740 A | 5/2007 | |
| KR | 100791931 B1 | 1/2008 | |
| KR | 1020080007333 A | 1/2008 | |
| WO | 2009132740 A2 | 5/2009 | |
| WO | WO2012/079159 * | 6/2012 | ............. G02F 1/01 |

OTHER PUBLICATIONS

Xu et al., "Structures of Orthoborate Anions and Physical Properties of Their Lithium Salt Nonaqueous Solutions," Journal of the Electrochemical Society, 150(1) E74-E80, 2003.*
Shkrob et al., "Charge Trapping in Imidazolium Ionic Liquids," J. Phys. Chem. B 113, 5582-5592, 2009.*
International Search Report for PCT/KR2011/010082 dated Jul. 25, 2012.
International Preliminary Report on Patentability and Written Opinion for PCT/KR2011/010082 dated Jul. 11, 2013.
International Preliminary Report on Patentability and Written Opinion for PCT/KR2011/010082 dated Jul. 11, 2013 (English Translation).

* cited by examiner

*Primary Examiner* — Paul A Zucker
*Assistant Examiner* — Mark Luderer
(74) *Attorney, Agent, or Firm* — Heslin Rothenberg Farley & Mesiti P.C.

(57) ABSTRACT

Disclosed are a novel diimmonium-based compound that has low light absorption in visible light region and has superior light absorption efficiency in near infrared region, and has superior durability and weatherability, and a near infrared absorption filter using the same. The diimmonium-based compound is represented by the formula 1 of claim 1.

2 Claims, 1 Drawing Sheet

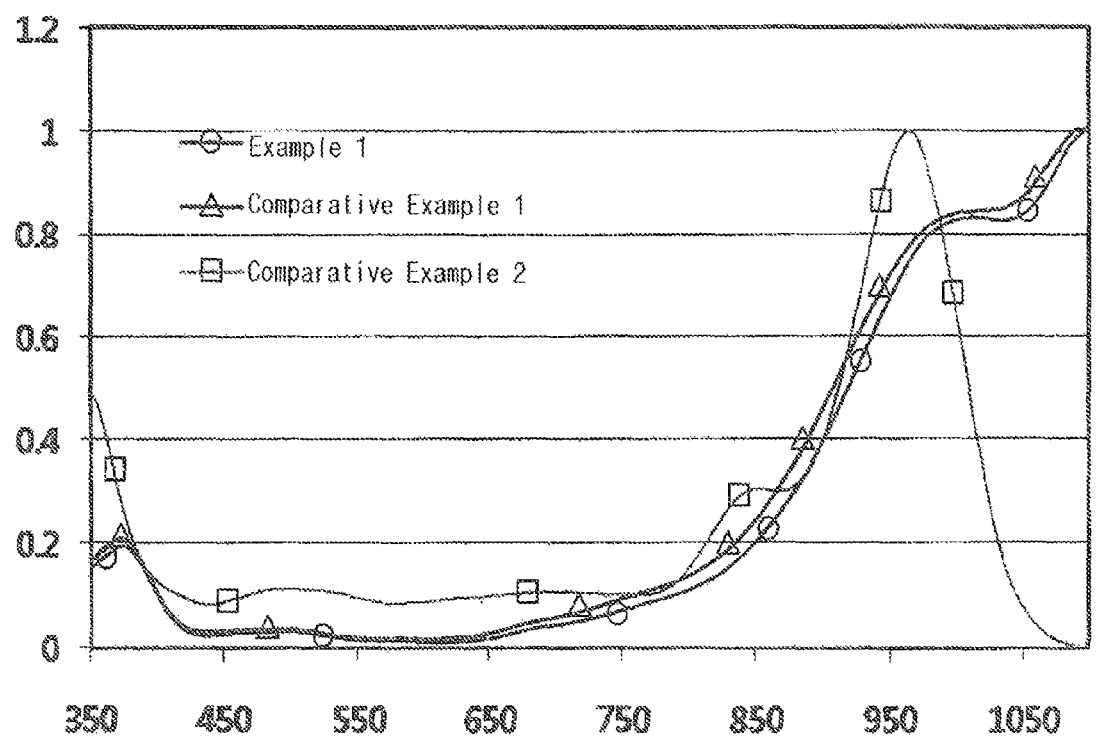

DIIMMONIUM-BASED COMPONENT AND NEAR INFRARED ABSORPTION FILTER USING SAME

CROSS REFERENCE TO RELATED APPLICATION

This application is the National Phase filing of International Application No. PCT/KR2011/010082, filed Dec. 26, 2011, which claims priority to Korean Application No. 10-2010-0136942, filed Dec. 28, 2010. The entire content of each prior application is hereby incorporated by reference.

TECHNICAL FIELD

The present invention relates to a diimmonium-based compound and a near infrared absorption filter using the same, and more particularly, to a novel diimmonium-based compound that has low light absorption in visible light region, but has superior light absorption efficiency in near infrared region, and has superior durability and weatherability, and a near infrared absorption filter using the same.

BACKGROUND ART

Energy saving materials are actively developed and applied in all industry area due to the situation of energy source which reached the limit. In general, a near infrared ray absorbing material (pigment) is used in order to prevent electronic devices from malfunctioning by interrupting the near infrared ray generated in the electronic devices. However, when attaching a film containing the material to a window, it can absorb part of sunlight, thereby reducing heat exchange between inside and outside, and thus prevent excessive rise and drop in room temperature. Accordingly, such a near infrared absorbing material can be used as a representative energy saving material, and is actively applied in construction and automobile industry. The near infrared absorbing material used in the film to be attached to a window of an automobile or a construction should have superior performance in absorbing the near infrared ray simultaneously with minimum absorbance at visible light region. That is because when a near infrared absorbing material having high absorbance at visible light region is used in the film to be attached to a window of an automobile or a construction, the automobile driver's view may become blurred or the house may command a bad view, and additional energy for internal light collection may be demanded or its color may be not natural.

Representative near infrared absorbing materials (pigments) include a diimmonium-based material (compound), a phthalocyanine-based material, a cyanine-based material and a metal dithiolene-based material, etc. However, there are little material that can be applied to a window and an electronic devices, etc. of a real automobile or a construction due to their physical or chemical properties in addition to the optical properties. The phthalocyanine-based material, which is the representative near infrared absorbing material, is actively applied for electronic devices including display due to its chemical stability. But the phthalocyanine-based material has a drawback in that it cannot be applied alone for a film, etc. for an automobile window because it has high absorbance in visible light region. The cyanine-based material has a drawback in that it has low chemical stability, and has narrow widths of the near infrared region which it can absorb alone, thus for actual application, the absorbing regions should be widened by mixing several materials. Further, the metal dithiolene-based material absorbs near infrared ray highly, but has a drawback in that it requires dispersion equipments, etc. for applying to a film due to its low solubility and is difficult to apply for a use requiring high transmittance.

However, the diimmonium-based material has characteristics that it absorbs near infrared ray at wide region, and hardly absorbs at the whole region of visible light, and thus even only single material can absorb the whole region of near infrared ray. Further, the diimmonium-based material has been often used conventionally in the window market of an automobile and a house since it has chemical stability and superior solubility to various organic solvent, and thus is easy to apply to a process. The main construction of the diimmonium-based near infrared absorbing material is comprised of cations having diimmonium structure and various anions. Representative anions include a halogen ion such as fluorine, chlorine and bromine, an inorganic-atom-containing ion such as hexafluoroantimonate ion, hyperchlorate ion and tetrafluoroborate ion, and an organic carbonate ion such as acetate ion and lactate ion, and these were initially used. Recently, an anion such as bis(trifluoromethanesulfonyl)imide ion and bis(pentafluoroethanesulfonyl) imide ion is much used. However, the diimmonium-based compounds which use the halogen ions as anions are difficult to apply to the process which uses them as a near infrared absorbing material, due to solubility problem. The organic carbonate ion is difficult to use actually since its solubility to water is high, thereby rendering yield control difficult in producing the diimmonium-based compound, and causing weatherability problem to a product. Further, anion material which is recently used widely, for example, the fluoroantimonic acid ions can be used as a near infrared absorbing material by their proper properties, but is not proper to use in a place closely related to human residential environment such as a house and an automobile since toxic material such as hydrofluoric acid can be emitted due to the fluorine atom present in the material, and the durability of the product (film, etc.) can be reduced by hydrofluoric acid.

DISCLOSURE

Technical Problem

Accordingly, it is an object of the present invention to provide a diimmonium-based compound that has wide and uniform light absorption efficiency at near infrared region (particularly, a wavelength range of 750 to 1,100 nm) and superior transmittance characteristics at visible light region (a wavelength range of 400 to 750 nm), and has superior durability and weatherability.

It is also an object of the present invention to provide a diimmonium-based compound which is eco-friendly since it does not contain a fluorine atom in its structure.

Yet another object of the present invention is to provide a near infrared absorption filter which includes one or two kinds of diimmonium-based compounds as a near infrared absorbing pigment.

Technical Solution

To accomplish the above objects of the present invention, according to one aspect of the present invention, there is provided a diimmonium-based compound represented by the formula I

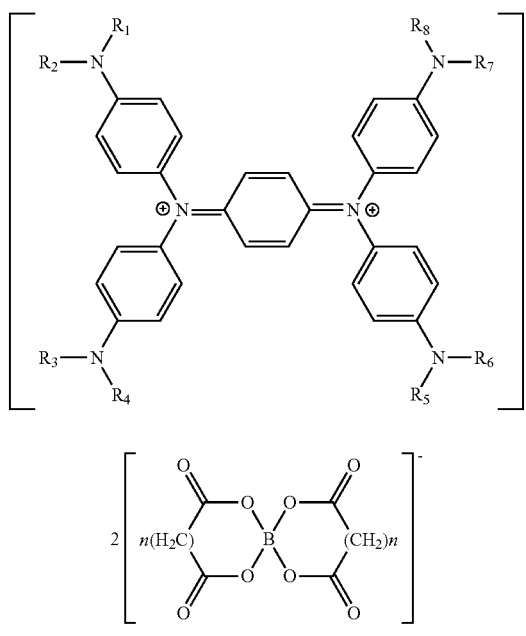

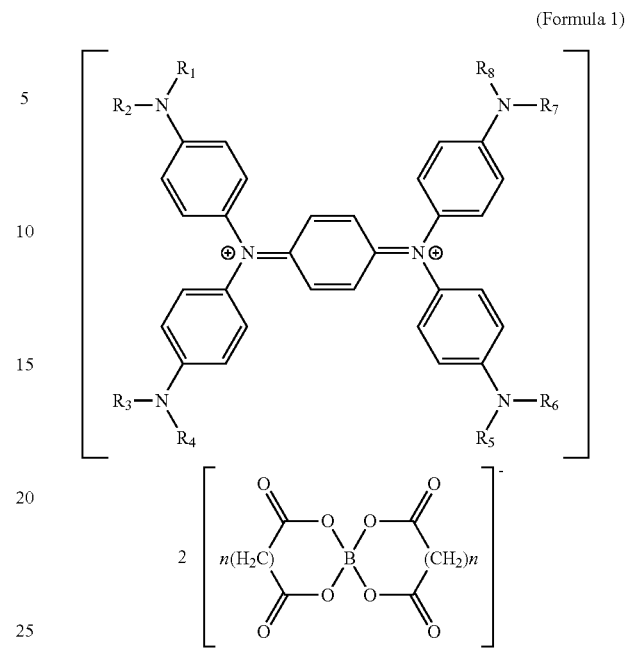
(Formula 1)

in which $R_1$ to $R_8$ independently represent a hydrogen atom (H), a substituted or unsubstituted alkyl group having 1 to 10 carbon atoms or a substituted or unsubstituted aryl group having 6 to 14 carbon atoms, and n is 0 or 1.

According to another aspect of the present invention, there is also provided a near infrared absorption filter which includes the diimmonium-based compounds.

Advantageous Effects

The diimmonium-based compound according to the present invention has unique optical characteristics of the diimmonium-based near infrared absorbing material, i.e., wide and uniform light absorption efficiency at near infrared region (particularly, a wavelength range of 750 to 1,100 nm) and has superior transmittance characteristics at visible light region (a wavelength range of 400 to 750 nm), and has superior durability and weatherability, and nonetheless does not contain a fluorine atom in its structure, and thus is useful as a near infrared absorbing material for an eco-friendly house and an automobile.

DESCRIPTION OF DRAWINGS

FIG. 1 depicts the UV/VIS absorption spectrum of the diimmonium-based compounds prepared according to the Example 1 of the present invention and Comparative examples 1 to 2.

BEST MODE

The present invention is explained in detail as follows.

A diimmonium-based compound according to present invention is represented by the formula I in which $R_1$ to $R_8$ independently represent a hydrogen atom (H), a substituted or unsubstituted alkyl group having 1 to 10 carbon atoms, preferably a substituted or unsubstituted alkyl group having 1 to 6 carbon atoms, or a substituted or unsubstituted aryl group having 6 to 14 carbon atoms, preferably a substituted or unsubstituted aryl group having 6 to 10 carbon atoms, e.g., a substituted or unsubstituted phenyl group, and n is 0 or 1. The substituents of $R_1$ to $R_8$ include an alkyl group having 1 to 5 carbon atoms, and a halogen excluding fluorine, etc.

A diimmonium-based compound according to present invention can be prepared by a known process of preparing a diimmonium-based compound, for example, prepared by applying the process described in the examples below.

The diimmonium-based compound according to the present invention has wide and uniform light absorption efficiency at near infrared region (particularly, a wavelength range of 750 to 1,100 nm) and has superior transmittance characteristics due to low absorbance at visible light region (a wavelength range of 400 to 750 nm). In particular, since the thermal stability of anion material thereof is very high and it does not contain a fluorine atom in its structure, the environment and durability problems due to generation of hydrofluoric acid do not occur. Further, since even only single diimmonium-based compound exhibits wide absorption at near infrared region, a single compound or a mixture of two kinds of compounds can obtain sufficient near infrared absorption when preparing a near infrared absorption filter, and thus the decrease in the compatibility between each diimmonium-based compound and a binder material, and the compatibility between diimmonium-based compounds is improved.

The diimmonium-based compound according to the present invention can be used as a pigment of a near infrared absorption filter in preparing the near infrared absorbing filter according to a conventional method. A polymer resin (binder material) suitable for the near infrared absorption filter include most of transparent polymer resins such as polymethylmethacrylate, polyester, polycarbonate and polyurethane, etc., but a material suitable for a condition such as heat resistance and environment resistance, etc. required according to each use can be used. The near infrared absorption filter can be prepared by dissolving the near infrared absorbing pigment in a solvent, and coating the solution on the polymer resin, and various solvents such as methylethylketone, tetrahydrofuran, chloroform and toluene, etc. can be used as the solvent.

[Mode for Invention]

Hereinafter, the present invention will be described in greater detail with reference to the following examples and the comparative examples. The following examples are for illustrative purposes and are not intended to limit the scope of the invention.

EXAMPLE 1

Preparation of a Diimmonium-Based Compound (N,N,N',N'-tetrakis(p-diisobutylaminophenyl)-p-phenylenediimmonium)

12g of N,N,N',N'-tetrakis(4-aminophenyl)-1,4-phenylenediamine, 40 g of isobutylbromide and 18 g of sodium bicarbonate were added to 3 neck flask equipped with a reflux apparatus, and then 30 g of N-methylpyrrolidone was added, and the mixture was reacted with stirring for 9 hours at 80° C. After reaction was completed, 300 g of dichloromethane and 1 L of water were added to the flask, and then stirred for 30 minutes. After stirring, separated dicholoromethane layer was distilled with a vacuum distiller to obtain 30 g of N,N,N',N'-tetrakis(p-diisobutylaminophenyl)-p-phenylenediamine (crude reactants).

30 g of the crude reactants were added to 3 neck flask equipped with a reflux apparatus, and then 15 g of lithiumbisoxalatoborate, 150 g of dichloromethane and 60 g of ethanol were added, and the mixture was refluxed for 2 hours. Then, 10 g of sodium persulfate and 200 g of water were added, and then refluxed for 2 hours. After reflux was completed, 250 g of dichloromethane and 300 g of water were added to the reaction flask, and then separated dicholoromethane layer was distilled with a vacuum distiller to obtain 10 g of biso(xalato)borate N, N, N',N'-tetrakis(p-diisobutylaminophenyl)-p-phenylenediimmonium, which is a diimmonium-based compound.

EXAMPLE 2

Preparation of a Diimmonium-Based Compound (bis(malonato)borate N,N,N',N'-tetrakis(p-diisobutylaminophenyl)-p-phenylene diimmonium)

30 g of N,N,N',N'-tetrakis(p-diisobutylaminophenyl)-p-phenylenediamine obtained by the same method as Example 1, 15 g of lithiumbismalonatoborate, 150 g of dichloromethane and 60 g of isobutanol were added, and then refluxed for 2 hours, and then 10 g of sodium persulfate and 200 g of water were further added, and then refluxed for 2 hours. After reflux was completed, 250 g of dichloromethane and 300 g of water were further added to the reaction flask, and then separated dicholoromethane layer was distilled with a vacuum distiller to obtain 8 g of bis(malonato)borate N,N,N',N'-tetrakis(p-diisobutylaminophenyl)-p-phenylenediimmonium, which is a diimmonium-based compound.

COMPARATIVE EXAMPLE 1

Preparation of a Diimmonium-Based Compound (bistrifluoromethanesulfonylimide N,N,N',N,-tetrakis(p-diisobutylamino phenyl)-p-phenylenediimmonium)

30 g of N,N,N',N'-tetrakis(p-diisobutylaminophenyl)-p-phenylenediamine obtained by the same method as Example 1, 15 g of lithiumbistrifluoromethanesulfonylimide, 150 g of dichloromethane and 60 g of ethanol were added, and then refluxed for 2 hours, and then 10 g of sodium persulfate and 200 g of water were further added, and then refluxed for 2 hours. After reflux was completed, 250 g of dichloromethane and 300 g of water were further added to the reaction flask, and then separated dicholoromethane layer was distilled with a vacuum distiller to obtain 10 g of bistrifluoromethanesulfonylimide N,N,N',N'-tetrakis(p-diisobutylaminophenyl)-p-phenylenediimonium), which is a diimmonium-based compound.

COMPARATIVE EXAMPLE 2

Preparation of a Vanadyl Phthalocyanine Compound 10 g of 3,4,5,6-tetrafluorophthalonitrile, 10 g of thiophenol and 7 g of potassium fluoride were added to 3 neck flask equipped with a reflux apparatus, and then 30 ml of acetonitrile was added as a solvent, and the mixture was reacted with stirring for 12 hours at room temperature. After reaction was completed, 7 g of 2,6-dimethylphenol and 4 g of potassium fluoride were added to the reacting solution, and then refluxed for 8 hours. After reaction was completed, the solution was distilled with a vacuum distiller. 20 g of crude reactants obtained as above were added to 3 neck flask equipped with a reflux apparatus, and refluxed with 2 g of vanadium trichloride, 2 g of 1-octanol and 30 g of benzonitrile for 8 hours. After reaction was completed, the solution was distilled with a vacuum distiller to obtain a vanadyl (vanadium oxide) phthalocyaniene (VOPc: Oxo-Vanadium Phthalocyanine)-based precursor compound VOPc(PhS)$_8${2,6-(CH$_3$)$_2$PhO}$_4$F$_4$. 10 g of the vanadyl phthalocyanine-based precursor compound and 50 ml of cyclohexylamine were added to 3 neck flask equipped with a reflux apparatus, and reacted for 8 hours at 60° C. After reaction was completed, the reacting solution was concentrated in vacuum to obtain a vanadyl phthalocyanine compound VOPc(PhS)$_8${2,6-(CH$_3$)$_2$PhO}$_4$ (C$_6$H$_{11}$NH)$_4$ (Ph=phenyl; in the formula 2 below, A$_2$, A$_3$, A$_6$, A$_7$, A$_{10}$, A$_{11}$, A$_{14}$ and A$_{15}$ are PhS; A$_1$, A$_5$, A$_9$ and A$_{13}$ are {2,6-(CH$_3$)$_2$PhO}; and A$_4$, A$_8$, A$_{12}$ and A$_{16}$ are C$_6$H$_{11}$NH) represented by the formula 2

[Formula 2]

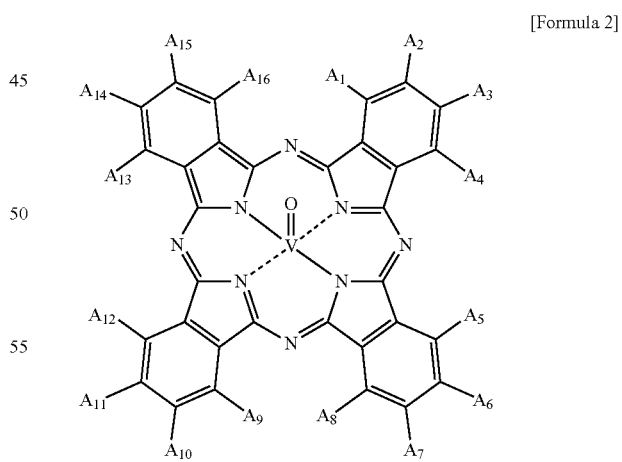

Experimental Example

UV/VIS Spectrum Analysis

The diimmonium-based compound and the vanadyl phthalocyanine compound prepared in the Example 1 and 2 and the Comparative example 1 and 2 were diluted in toluene, respectively, and UV/VIS spectrum therefor was measured. The maximum absorption wavelength of the diimmonium-based compound of the Example 1 and 2 and the Comparative example 1 was longer than 1000 nm, and the maximum absorption wavelength of the vanadyl phthalocyanine compound of the Comparative example 2 was 932 nm. Further, the US/VIS absorption spectrum of the diimmonium-based compound and the vanadyl phthalocyanine compound prepared in the Example 1 and the Comparative example 1 and 2 was depicted in FIG. 1.

From the examples and FIG. 1, it can be ascertained that the diimmonium-based compound according to the present invention does not cause the environment and durability problems due to generation of hydrofluoric acid since the compound does not contain a fluorine atom (F) in its structure; and the compound has wide and uniform absorption efficiency at near infrared region (particularly, a wavelength range of 750 to 1100 nm), and has superior transmittance characteristics at visible light region (a wavelength range of 400 to 750 nm) compared to the vanadyl phthalocyanine compound prepared in the Comparative example 2.

[Industrial Applicability]

The diimmonium-based compound according to the present invention is useful as a near infrared absorption material for an eco-friendly house and an automobile.

The invention claimed is:

1. A diimmonium-based near infrared absorbing and visible light transmitting compound of formula I

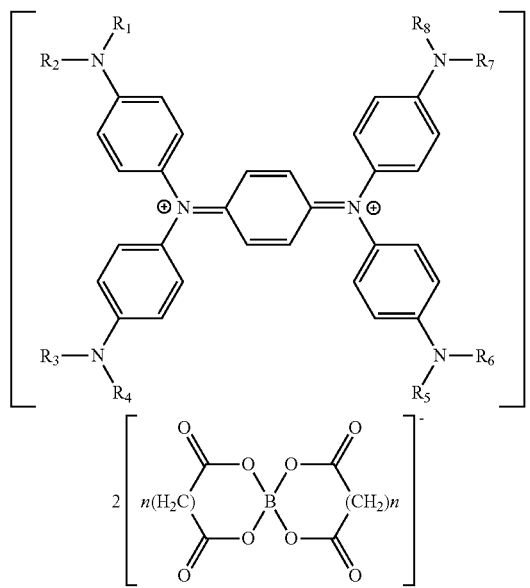

in which $R_1$ to $R_8$ independently represent a hydrogen atom (H), a substituted or unsubstituted alkyl group having 1 to 10 carbon atoms or a substituted or unsubstituted aryl group having 6 to 14 carbon atoms, and n is 0 or 1.

2. A near infrared absorbing and visible light transmitting filter comprising the diimmonium-based compound according to claim 1.

* * * * *